US009494553B2

(12) United States Patent
Tanaka et al.

(10) Patent No.: US 9,494,553 B2
(45) Date of Patent: Nov. 15, 2016

(54) ELECTROPHORESIS CHIP, ELECTROPHORESIS APPARATUS, AND METHOD FOR ANALYZING SAMPLE BY CAPILLARY ELECTROPHORESIS

(75) Inventors: Yoshihide Tanaka, Osaka (JP); Yusuke Nakayama, Kyoto (JP); Satoshi Yonehara, Kyoto (JP)

(73) Assignees: National Institute of Advanced Industrial Science and Technology, Tokyo (JP); ARKRAY, Inc., Kyoto (JP)

( * ) Notice: Subject to any disclaimer, the term of this patent is extended or adjusted under 35 U.S.C. 154(b) by 273 days.

(21) Appl. No.: 12/515,994

(22) PCT Filed: Apr. 28, 2008

(86) PCT No.: PCT/JP2008/058206
§ 371 (c)(1),
(2), (4) Date: Dec. 31, 2009

(87) PCT Pub. No.: WO2008/136465
PCT Pub. Date: Nov. 13, 2008

(65) Prior Publication Data
US 2010/0116660 A1    May 13, 2010

(30) Foreign Application Priority Data
Apr. 27, 2007  (JP) ................................ 2007-119262

(51) Int. Cl.
*G01N 27/447*    (2006.01)
(52) U.S. Cl.
CPC .. *G01N 27/44791* (2013.01); *G01N 27/44743* (2013.01)
(58) Field of Classification Search
CPC ..................... B01L 3/50273; B01L 3/502746; B01L 3/502769
USPC .......... 73/23.31, 195; 702/204; 60/279, 282, 60/284–288; 205/780.5, 284–288, 781, 205/783.5–785; 204/424–429
See application file for complete search history.

(56) References Cited

U.S. PATENT DOCUMENTS 5,858,195 A * 1/1999 Ramsey ........................ 204/601
6,685,809 B1 * 2/2004 Jacobson et al. ............. 204/450
(Continued)

FOREIGN PATENT DOCUMENTS

| CN | 1380538 A | 11/2002 | |
|---|---|---|---|
| EP | 1757926 | 2/2007 | ........... G01N 27/447 |

(Continued)

OTHER PUBLICATIONS

Berl et al. Agric. and Food Chem. V.2 No. 1, p. 37 (1954).*
(Continued)

*Primary Examiner* — Luan Van
*Assistant Examiner* — Steven Rosenwald
(74) *Attorney, Agent, or Firm* — Morgan, Lewis & Bockius LLP

(57) ABSTRACT

An electrophoresis chip that can be small and simple and that can analyze a sample with high accuracy is provided. The electrophoresis chip includes an upper substrate 4, a lower substrate 1, an introduction reservoir 2a, a recovery reservoir 2b and a capillary channel for sample analysis 3x. The introduction reservoir 2a and the recovery reservoir 2b are formed in the lower substrate 1. The introduction reservoir 2a and the recovery reservoir 2b are in communication with each other via the capillary channel for sample analysis 3x. The introduction reservoir 2a receives a sample to be measured. The sample is electrophoretically introduced directly into the capillary channel for sample analysis 3x by creating a potential difference between the introduction reservoir 2a and the recovery reservoir 2b, and is also analyzed in the capillary channel for sample analysis 3x during the separation of the sample while the sample is being continuously supplied.

11 Claims, 8 Drawing Sheets

(56) References Cited

U.S. PATENT DOCUMENTS

| | | | |
|---|---|---|---|
| 6,942,771 B1* | 9/2005 | Kayyem | 204/409 |
| 2002/0144907 A1 | 10/2002 | Yamamoto | |
| 2004/0084311 A1* | 5/2004 | Okamoto et al. | 204/450 |
| 2006/0177350 A1 | 8/2006 | Sano et al. | 422/100 |

FOREIGN PATENT DOCUMENTS

| | | | |
|---|---|---|---|
| JP | 8-178897 | 7/1996 | G01N 27/447 |
| JP | 2790067 | 8/1998 | |
| JP | 2005-077293 | 3/2005 | |
| JP | 3656165 | 6/2005 | |
| JP | 2005-207860 | 8/2005 | |
| JP | 2007-108181 | 4/2007 | |
| JP | 2008-164382 | 7/2008 | |
| JP | 2008-170351 | 7/2008 | |
| JP | 2008-164382 | 7/2009 | |
| JP | 2008-170350 | 7/2009 | |
| WO | WO 96/04547 | 2/1996 | G01N 27/00 |
| WO | WO 98/10122 | 3/1998 | C25B 9/00 |
| WO | WO 2005/106448 | 11/2005 | |
| WO | WO 2008/078781 | 7/2008 | |

OTHER PUBLICATIONS

Gao et al. (Anal. Chem. 1997, 69, 2945-2951).*
Mikkers (Anal. Chem. 1997, 69, 333-337).*
Gao, et al. "Measurement of the Binding of Proteins to Polyelectrolytes by Frontal Analysis Continuous Capillary Electrophoresis", Anal. Chem. 69:15, 2945-2951, 1997.
Extended European Search Report of the corresponding European Application (No. 08752216.5), dated Jul. 19, 2010.
Roper et al., "Microfluidic Chip for Continuous Monitoring of Hormone Secretion from Live Cells Using an Electrophoresis-Based Immunoassay", Analytical Chemistry 75(18): pp. 4711-4717 (2003).
Thomas et al., "Strategy for Repertitive Pinched Injections on a Microfluidic Device", Analytical Chemistry 76(20): pp. 6053-6057 (2004).
Office Action dated May 19, 2011 in the corresponding European Patent Application No. 08752216.5.
Summons to Attend Oral Proceedings issued in corresponding European Patent Application No. 08752216.5 dated Dec. 4, 2013.
Decision to refuse a European Patent application issued in corresponding European Patent Application No. 08752216.5 dated Apr. 16, 2014.
Extended European Search Report issued in corresponding European Patent Application No. 14173977.1 dated Oct. 22, 2014.
International Union of Pure and Applied Chemistry, Analytical Chemistry Division, Compendium of Analytical Nomenclature, Definitive Rules 1997, 9.2.3.3 The Chromatogram (http://old.iupac.org/publications/analytical_compendium).

* cited by examiner

FIG. 4
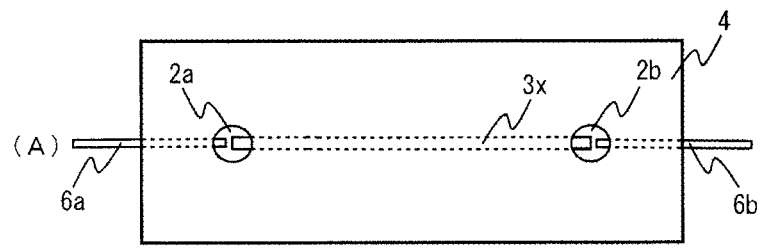
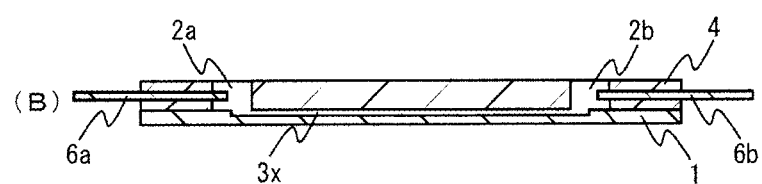
FIG. 5
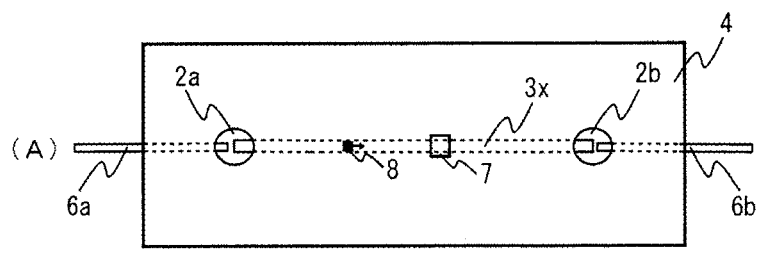
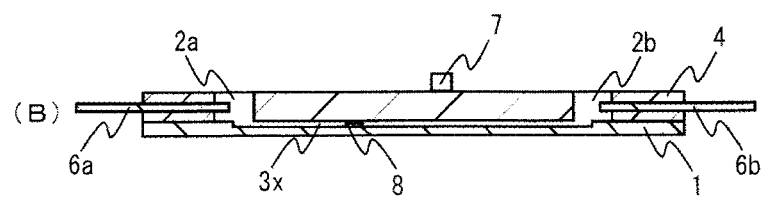

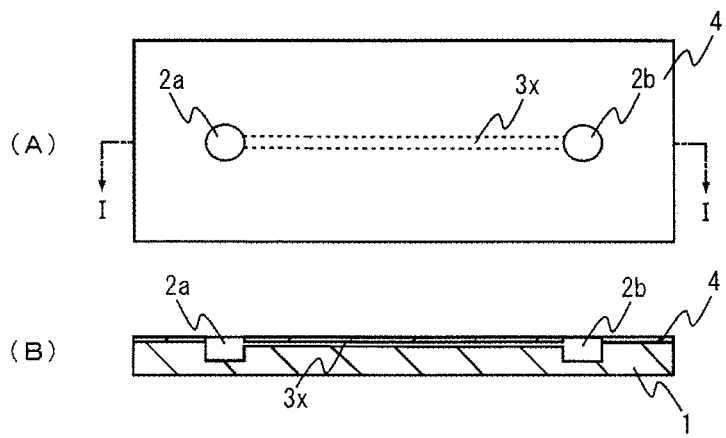
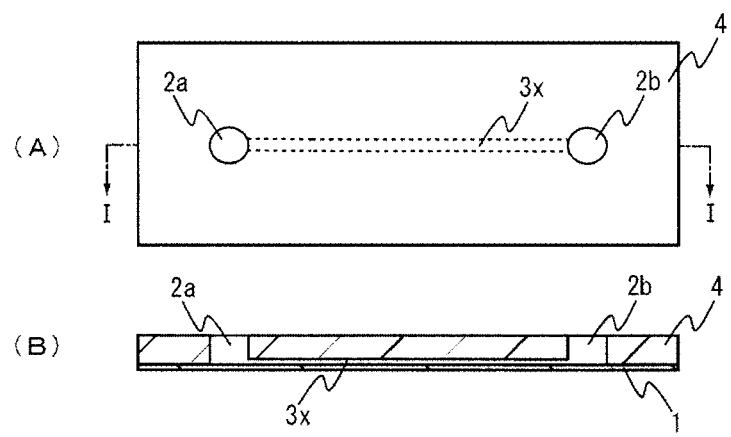
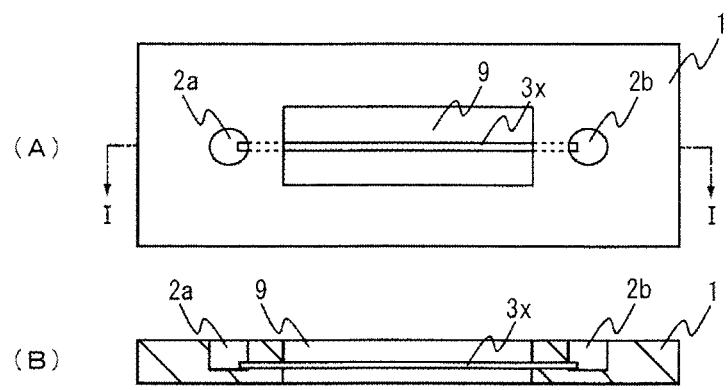

FIG. 9
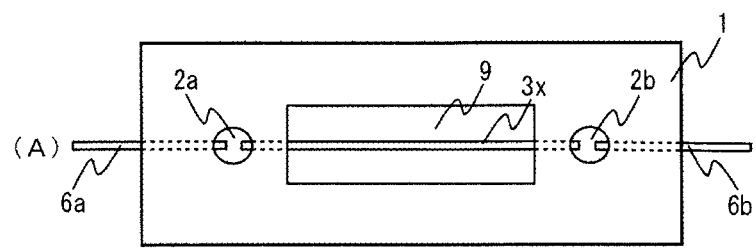
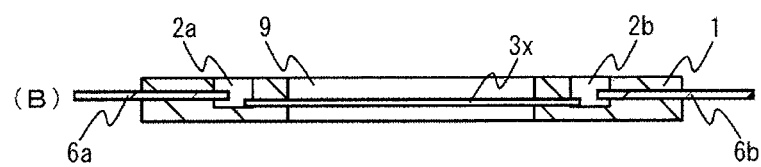
FIG. 10
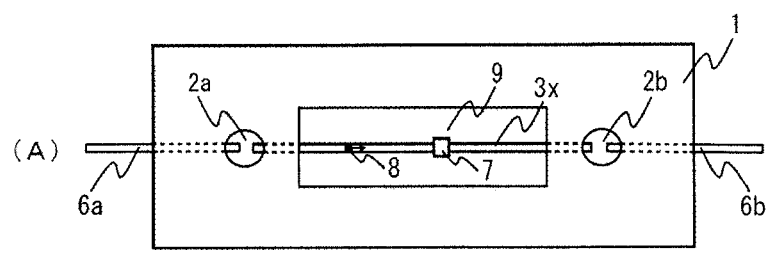
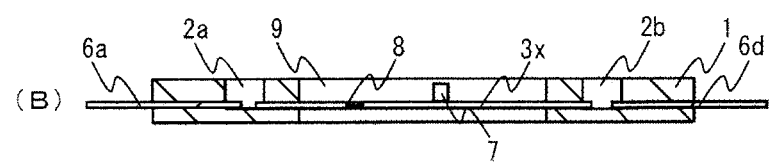

ELECTROPHORESIS CHIP, ELECTROPHORESIS APPARATUS, AND METHOD FOR ANALYZING SAMPLE BY CAPILLARY ELECTROPHORESIS

The present application is a U.S. National Phase Application of International Application No. PCT/JP2008/058206, filed Apr. 28, 2008, which claims the benefit of Japanese Patent Application No. 2007-119262, filed Apr. 27, 2007, both of which are hereby incorporated by reference in their entirety.

TECHNICAL FIELD

The present invention relates to an electrophoresis chip, an electrophoresis apparatus and a method for analyzing a sample by capillary electrophoresis.

BACKGROUND ART

The degree of glycosylation of various proteins has been analyzed as an indicator that shows the condition of a living body. In particular, because the degree of glycosylation of hemoglobin (Hb), especially HbA1c, in blood cells reflects the history of glucose levels in a living body, it is regarded as an important indicator in the diagnosis and treatment of diabetes. HbA1c is HbA($\alpha_2\beta_2$) whose $\beta$-chain N-terminal valine has been glycosylated.

HbA1c has been analyzed by, for example, immunological methods, enzymatic methods, and high-performance liquid chromatography (HPLC) methods, among others. Although immunological methods and enzymatic methods are generally used in processing and analyzing large numbers of specimens, they are of low accuracy when determining the risk of complications. In contrast, although HPLC methods have poorer processing capabilities than immunological methods or enzymatic methods, they are useful in determining the risk of complications. However, due to the configuration of HPLC methods, the analysis apparatus is very large and costly.

On the other hand, electrophoresis chips are used generally in the analyses of biologically-relevant samples (see, for example, Patent Documents 1 and 2). Compared with HPLC methods, such electrophoresis chips allow the analyzers to be small.

A conventional electrophoresis chip has two capillary channels, one for sample introduction and the other for sample analysis. The two capillary channels intersect each other in a cross shape and are in communication with each other at the intersection. An analysis of a sample using such an electrophoresis chip is carried out as follows. First, a sample to be analyzed is introduced into a capillary channel for sample introduction. Then, a potential difference is created between both ends of the capillary channel for sample introduction to move the sample to the intersection. Next, a potential difference is created between both ends of a capillary channel for sample analysis to move the sample from the intersection into the capillary channel where the analysis of the sample is carried out.

Electrophoresis chips that have cross-shaped capillary channels that are in communication with each other at the intersection have problems as follows. Firstly, the configuration of such capillary channels is complex. Secondly, a voltage applying device for creating a potential difference between both ends of the two capillary channels needs to be provided separately. For these reasons, there are limitations in making such electrophoresis chips smaller and simpler. When the target of voltage application is changed from the capillary channel for sample introduction to the capillary channel for sample analysis, sample diffusion cannot be fully controlled if the voltage (potential difference) is not controlled properly. It may be possible in such a case that the amount of a sample introduced into the capillary channel for sample analysis is not uniform. Moreover, if the components of a sample have greatly different migration speeds, the composition of the sample at different portions within the capillary channel for sample introduction may be different from that of the original sample. As a result, the composition of a sample introduced into the capillary channel for sample analysis may not be uniform. Use of a long sample-plug for introduction into the capillary channel for sample analysis to prevent this phenomenon may result in a problem in that the ability to separate exerted in the capillary channel for sample analysis is impaired.

Patent Document 1: Japanese Patent No. 2790067
Patent Document 2: Japanese Patent No. 3656165

DISCLOSURE OF INVENTION

Therefore, an object of the present invention is to provide an electrophoresis chip that can be small and simple and that can analyze a sample with high accuracy.

To achieve the above object, an electrophoresis chip of the present invention includes a substrate, an introduction reservoir, a recovery reservoir and a capillary channel,
the capillary channel comprises a capillary channel for sample analysis,
the introduction reservoir and the recovery reservoir are formed in the substrate,
the introduction reservoir and the recovery reservoir are in communication with each other via the capillary channel for sample analysis, and
the introduction reservoir receives a sample to be analyzed; and
the sample is electrophoretically introduced directly into the capillary channel for sample analysis by creating a potential difference between the introduction reservoir and the recovery reservoir, and is also analyzed in the capillary channel for sample analysis during the separation of the sample while the sample is being continuously supplied.

An electrophoresis apparatus of the present invention is an electrophoresis apparatus that includes an electrophoresis chip and an analysis unit, with the electrophoresis chip being an electrophoresis chip of the present invention.

A method of the present invention for analyzing a sample by capillary electrophoresis uses an electrophoresis chip of the present invention or an electrophoresis apparatus of the present invention, and the method includes:
an introduction step of introducing the sample into the introduction reservoir, and
an analysis step of electrophoretically introducing the sample directly into the capillary channel for sample analysis by creating a potential difference between the introduction reservoir and the recovery reservoir, and also analyzing the sample in the capillary channel for sample analysis during the separation of the sample while the sample is being continuously supplied.

An electrophoresis chip of the present invention is a chip wherein an introduction reservoir and a recovery reservoir are formed in a substrate, and the introduction reservoir and the recovery reservoir are in communication with each other via a capillary channel for sample analysis. In an electrophoresis chip of the present invention, a sample is electrophoretically introduced directly into the capillary channel for sample analysis by creating a potential difference between the introduction reservoir and the recovery reservoir, and the analysis of the sample is carried out in the capillary channel for sample analysis. That is, in an electrophoresis chip of the present invention, the capillary channel for sample analysis also serves as a capillary channel for sample introduction as found in conventional electrophoresis chips. Therefore, an electrophoresis chip of the present invention can be small and simple and can analyze a sample with high accuracy. Moreover, an electrophoresis chip of the present invention allows a sample to be continuously supplied to the capillary channel for sample analysis, thereby subjecting a relatively large amount of a sample to analysis (detection), and is thus also better in detection. Therefore, it is possible with an electrophoresis chip of the present invention to accurately analyze a sample in, for example, POC (point of care) testing, and thus to manage the risk of complications.

BRIEF DESCRIPTION OF DRAWINGS

FIG. 4 shows diagrams illustrating a configuration of another example of an electrophoresis chip of the present invention.

FIG. 5 shows a cross-sectional view illustrating a configuration of an example of an electrophoresis apparatus of the present invention.

FIG. 6 shows diagrams illustrating a configuration of still another example of an electrophoresis chip of the present invention.

FIG. 7 shows diagrams illustrating a configuration of still another example of an electrophoresis chip of the present invention.

FIG. 8 shows diagrams illustrating a configuration of still another example of an electrophoresis chip of the present invention.

FIG. 9 shows diagrams illustrating a configuration of still another example of an electrophoresis chip of the present invention.

FIG. 10 shows diagrams illustrating a configuration of another example of an electrophoresis apparatus of the present invention.

DESCRIPTION OF THE PREFERRED EMBODIMENTS

Figure 1:
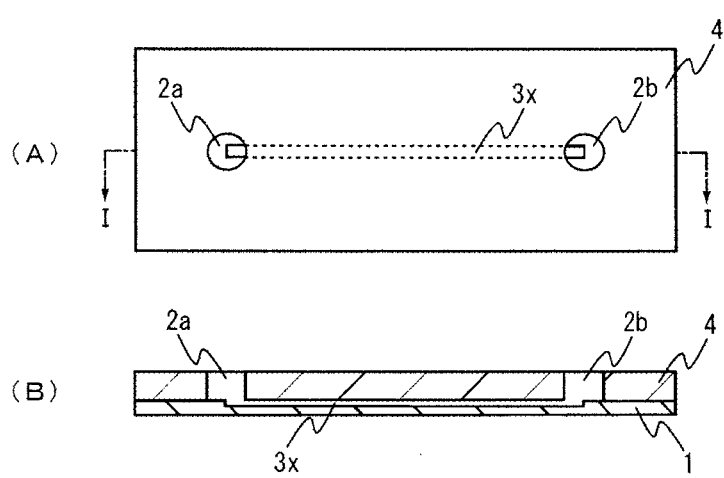
FIG. 1 shows diagrams illustrating a configuration of an example of an electrophoresis chip of the present invention.

In an electrophoresis chip of the present invention, the overall length of the chip is in a range of, for example, 10 to 200 mm and preferably in a range of 30 to 70 mm; the overall width of the chip is in a range of, for example, 10 to 60 mm; and the overall thickness of the chip is in a range of, for example, 0.3 to 5 mm. The overall length of the chip refers to the dimension of the longest portion of the chip in the longitudinal direction; the overall width of the chip refers to the dimension of the longest portion of the chip in a direction (width direction) perpendicular to the longitudinal direction; and the overall thickness of the chip refers to the dimension of the longest portion of the chip in a direction (thickness direction) perpendicular to both the longitudinal direction and the width direction.

In an electrophoresis chip of the present invention, it is preferable that the capillary channel is filled with an electrophoresis running buffer.

In an electrophoresis chip of the present invention, the diameter of the capillary channel is in a range of, for example, 10 to 200 µm and preferably in a range of 25 to 100 µm; and the length thereof is in a range of, for example, 0.5 to 15 cm. When the shape of the cross section of the capillary channel is not circular, the diameter of the capillary channel refers to the diameter of a circle having an area that corresponds to the cross sectional area of a portion having the largest cross-sectional area.

In an electrophoresis chip of the present invention, the inner wall of a capillary channel may be coated with a cationic group-containing compound. Examples of the cationic group-containing compound include compounds that contain cationic groups and reactive groups. Preferable examples of the cationic groups include amino groups and ammonium groups. A preferable example of the cationic group-containing compound is a silylating agent that contains at least an amino group or an ammonium group. The amino groups may be any of the primary, secondary and tertiary amino groups.

Examples of the silylating agent include
N-(2-diaminoethyl)-3-propyltrimethoxysilane,
aminophenoxydimethylvinylsilane, 3-aminopropyldiisopropylethoxysilane,
3-aminopropylmethylbis(trimethylsiloxy)silane,
3-aminopropylpentamethyldisiloxane, 3-aminopropylsilanetriol,
bis(p-aminophenoxy)dimethylsilane,
1,3-bis(3-aminopropyl)tetramethyldisiloxane,
bis(dimethylamino)dimethylsilane, bis(dimethylamino)vinylmethylsilane,
bis(2-hydroxyethyl)-3-aminopropyltriethoxysilane,
3-cyanopropyl(diisopropyl)dimethylaminosilane,
(aminoethylaminomethyl)phenethyltrimethoxysilane,
N-methylaminopropyltriethoxysilane, tetrakis(diethylamino)silane,
tris(dimethylamino)chlorosilane, and tris(dimethylamino)silane, among others.

Among such silylating agents, those in which silicon atom(s) are substituted with titanium or zirconium may be used. Such silylating agents may be used singly or may be used in a combination of two or more.

Coating of the inner wall of a capillary channel with a silylating agent is performed, for example, as follows. First, a silylating agent is dissolved or dispersed in an organic solvent to prepare a treatment fluid. Examples of organic solvents for use in the preparation of the treatment fluid may be dichloromethane, toluene and the like. The concentration of the silylating agent in the treatment fluid is not particularly limited. This treatment fluid is passed through a capillary channel, and then heated. Due to this heating, the silylating agent is bonded to the inner wall of the capillary channel by covalent bonding, resulting in a cationic group being disposed on the inner wall of the capillary channel. Thereafter, washing (after-treatment) is performed with at least an organic solvent (dichloromethane, methanol, acetone, or the like), an acid solution (phosphoric acid, or the like), an alkaline solution, or a surfactant solution. Although this washing is optional, it is preferable to perform such washing. Moreover, when a capillary tube that is a member independent of the substrate serves as the capillary channel, a capillary tube whose inner wall is coated with the cationic group-containing compound through the use of a commercially available silylating agent of an aforementioned kind may be used.

It is preferable that an anionic layer formed from an anionic group-containing compound is further laminated on the inner wall of the capillary channel that has been coated with the cationic group-containing compound. It is thus possible to prevent hemoglobin, or the like present in a sample that will be described below from being adsorbed onto the inner wall of a capillary channel. Moreover, due to the formation of a complex between the sample and the anionic group-containing compound and due to the electrophoresis thereof, separation efficiency is enhanced compared with the electrophoresis of sample alone. As a result of these, analysis of glycosylated hemoglobin, or the like can be performed more accurately in a shorter period of time. An anionic group-containing polysaccharide is preferable as the anionic group-containing compound that forms a complex with the sample. Examples of anionic group-containing polysaccharide include sulfated polysaccharides, carboxylated polysaccharides, sulfonated polysaccharides and phosphorylated polysaccharides. Among these, sulfated polysaccharides and carboxylated polysaccharides are preferable. The sulfated polysaccharide is preferably chondroitin sulfate, or heparin, among others, with chondroitin sulfate being particularly preferable. The carboxylated polysaccharides are preferably alginic acid and salts thereof (for example, sodium alginate). There are seven types of chondroitin sulfate, i.e., chondroitin sulfate A, chondroitin sulfate B, chondroitin sulfate C, chondroitin sulfate D, chondroitin sulfate E, chondroitin sulfate H, and chondroitin sulfate K, and any of these types may be used. The anionic layer can be formed by, for example, bringing a fluid that contains the anionic group-containing compound into contact with the inner wall of a capillary channel that has been coated with a cationic group-containing compound. In this case, although a fluid for forming an anionic layer may be prepared separately, it is preferable in terms of operation efficiency that an electrophoresis running buffer that contains the anionic group-containing compound is prepared and is passed through the capillary channel whose inner wall is coated with a cationic group-containing compound.

The electrophoresis running buffer is not particularly limited, and an electrophoresis running buffer that uses an organic acid is preferable. Examples of organic acids include maleic acid, tartaric acid, succinic acid, fumaric acid, phthalic acid, malonic acid, and malic acid, among others. Preferably, the electrophoresis running buffer contains a weak base. Examples of weak bases include arginine, lysine, histidine, and tris, among others. The pH of the electrophoresis running buffer is in a range of, for example, 4.5 to 6. In the electrophoresis running buffer, the concentration of an anionic group-containing compound is in a range of, for example, 0.001 to 10 wt %.

In connection with an electrophoresis chip of the present invention, the sample may be whole blood, the electrophoresis chip may include a pretreatment reservoir for hemolyzing and diluting the sample, and the pretreatment reservoir and the introduction reservoir may be in communication with each other.

In connection with an electrophoresis chip of the present invention, it is preferable that the sample contains at least glycosylated hemoglobin or glucose. The glycosylated hemoglobin is not particularly limited, and examples include HbA1c, unstable HbA1c, and GHbLys, among others, with HbA1c being particularly preferable.

An electrophoresis chip of the present invention may be configured such that:
a glucose analysis unit is formed at one end of the capillary channel for sample analysis,
the recovery reservoir is formed at the other end of the capillary channel for sample analysis,
the introduction reservoir is formed between the glucose analysis unit and the recovery reservoir, and
the glucose analysis unit and the introduction reservoir, as well as the introduction reservoir and the recovery reservoir, are in communication via the capillary channel for sample analysis.

An electrophoresis chip of the present invention may be configured such that:
the substrate includes an upper substrate and a lower substrate,
two through-holes are formed in the upper substrate,
a groove is formed in the lower substrate,
the upper substrate is laminated onto the lower substrate,
spaces created by sealing the bottom parts of the two through-holes formed in the upper substrate with the lower substrate serve as the introduction reservoir and the recovery reservoir, and
a space created by sealing the upper part of the groove formed in the lower substrate with the upper substrate serves as the capillary channel for sample analysis.

An electrophoresis chip of the present invention may be configured such that:
the electrophoresis chip further includes a sealing material,
two through-holes are formed in the substrate,
a groove is formed in the bottom surface of the substrate,
the bottom surface of the substrate is sealed with the sealing material,
spaces created by sealing the bottom parts of the two through-holes formed in the substrate with the sealing material serve as the introduction reservoir and the recovery reservoir, and
a space created by sealing the lower part of the groove formed in the bottom surface of the substrate with the sealing material serves as the capillary channel for sample analysis.

An electrophoresis chip of the present invention may be configured such that the introduction reservoir and the recovery reservoir are in communication with each other via a capillary tube that is a member independent of the substrate, and the capillary tube may serve as the capillary channel for sample analysis. The material of the capillary tube is not particularly limited. Examples of the material for the capillary tube include glass, fused silica, and plastics, among others. The glass or fused silica capillary tubes used may be commercially available products. The plastic capillary tubes used may also be commercially available products, and examples include capillary tubes made from, for example, polymethylmethacrylate (PMMA), polycarbonate, polystyrene, polytetrafluoroethylene (PTFE), and polyether ether ketone (PEEK), among others.

In an electrophoresis chip of the present invention, the volumes of the introduction reservoir and the recovery reservoir are not particularly limited, and are each in a range of, for example, 1 to 1000 mm$^3$ and preferably in a range of 50 to 100 mm$^3$.

In an electrophoresis chip of the present invention, the introduction reservoir and the recovery reservoir may each have an electrode for use with a capillary electrophoresis method.

In a method of the present invention for analyzing a sample by capillary electrophoresis, it is preferable that, in the introduction step, a diluted sample (sample is diluted with an electrophoresis running buffer) is introduced into the introduction reservoir, and the volume ratio of the sample: the electrophoresis running buffer is in a range of 1:4 to 1:99. The volume ratio of the sample: the electrophoresis running buffer is more preferably in a range of 1:9 to 1:49 and still more preferably in a range of 1:19 to 1:29.

In a method of the present invention for analyzing a sample by capillary electrophoresis, the analysis of the sample in the analysis step may be carried out by, for example, arithmetic processing of the absorbance of the sample. It is preferable in this case that the arithmetic processing of absorbance involves at least differential processing or difference processing to give a pherogram, and the proportion of a component in the sample is obtained by calculating at least a peak height or a peak area in the pherogram.

Next, an electrophoresis chip of the present invention is described with reference to embodiments. The present invention, however, is not limited to the embodiments presented below.

Embodiment 1

FIG. 1 shows an example of an electrophoresis chip of the present invention. FIG. 1(A) is a plan view of an electrophoresis chip of this embodiment, and FIG. 1(B) is a cross-sectional view when taken along I-I of FIG. 1(A). For easier understanding, the size, proportions and like features of each component in the illustrations are different from the actual features of each component. This electrophoresis chip is, as shown in the figure, configured such that an upper substrate 4 is laminated onto a lower substrate 1. Two through-holes are formed in the upper substrate 4. The bottom parts of the two through-holes formed in the upper substrate 4 are sealed with the lower substrate 1 and, thus, an introduction reservoir 2a and a recovery reservoir 2b are formed. An I-shaped groove is formed in the lower substrate 1. By sealing the upper part of the I-shaped groove formed in the lower substrate 1 with the upper substrate 4, a capillary channel for sample analysis 3x is formed. The introduction reservoir 2a and the recovery reservoir 2b are in communication with each other via the capillary channel for sample analysis 3x. An electrophoresis chip of this embodiment is rectangular parallelepipedic. However, the present invention is not limited thereto. A capillary electrophoresis chip of the present invention may be in any shape insofar as it does not adversely affect the analysis of a sample, which will be described below. The planar shape of an electrophoresis chip of this embodiment is rectangular. However, the present invention is not limited thereto. The planar shape of an electrophoresis chip of the present invention may be, for example, square or may be of another form. An electrophoresis chip of this embodiment includes two substrate pieces (upper substrate 4 and lower substrate 1). However, an electrophoresis chip of the present invention is not limited thereto. An electrophoresis chip of the present invention may be composed of, for example, a single-piece substrate as described below.

Next, a method for producing an electrophoresis chip of this embodiment is described. However, the electrophoresis chip may be produced by methods other than the production method described below.

In an electrophoresis chip of this embodiment, a substrate formed from, for example, a glass material, a polymeric material, or the like can be used as the lower substrate 1. Examples of the glass material include synthetic silica glass, and borosilicate glass, among others. Examples of polymeric materials include PMMA, cycloolefin polymer (COP), polycarbonate (PC), polydimethylsiloxane (PDMS), polystyrene, and polylactic acid, among others.

In an electrophoresis chip of this embodiment, the length and the width of the lower substrate 1 correspond to the overall length and the overall width of the chip, as described above. Therefore, the length and the width of the lower substrate 1 are arranged to be identical to the overall length and the overall width of the chip, as described above. The thickness of the lower substrate 1 in an electrophoresis chip of this embodiment is in a range of, for example, 0.1 to 3 mm and preferably in a range of 0.1 to 1 mm.

The material of the upper substrate 4 is not particularly limited insofar as it does not adversely affect an absorbance measurement that will be described below. For example, an upper substrate 4 that is formed from the same material as the lower substrate 1 can be used.

The length and the width of the upper substrate 4 are the same as the length and the width of the lower substrate 1, respectively. The thickness of the upper substrate 4 is suitably determined according to the volumes or like factors of the introduction reservoir 2a and the recovery reservoir 2b and, for example, it is in a range of 0.1 to 3 mm and preferably in a range of 1 to 2 mm.

The width and the depth of the capillary channel for sample analysis 3x are, for example, a width is in a range of 25 to 200 μm and a depth is in a range of 25 to 200 μm, and preferably a width is in a range of 40 to 100 μm and a depth is in a range of 40 to 100 μm.

The volumes of the introduction reservoir 2a and the recovery reservoir 2b are as described above. In FIG. 1, the shapes of the introduction reservoir 2a and the recovery reservoir 2b are cylindrical. However, an electrophoresis chip of the present invention is not limited to this. In an electrophoresis chip of the present invention, the shapes of the introduction reservoir 2a and the recovery reservoir 2b are not particularly limited insofar as the introduction and the recovery of a sample are not adversely affected, which will be described below and, for example, the reservoirs can be in any shape such as a quadrangular prism, a quadrangular pyramid, a cone, or a combination of these shapes. Furthermore, the volumes and the shapes of the introduction reservoir 2a and the recovery reservoir 2b may all be the same or may each be different.

In an electrophoresis chip of this embodiment, the overall thickness of the chip is the sum of the thickness of the lower substrate 1 and the thickness of the upper substrate 4. The overall thickness of the chip is as described above.

For example, when the material of the lower substrate 1 is glass, the electrophoresis chip can be produced as follows.

First, a surface of a glass plate 20 is masked with an alloy 21 of chromium and gold as shown in FIG. 2(A). A surface of the alloy 21 is then coated with a photoresist 22.

Next, a photosensitive film on which a layout pattern for a capillary channel for sample analysis 3x is drawn is adhered to a surface of the photoresist 22 as shown in FIG. 2(B) to prepare a photomask 23. Ultraviolet rays 24 are then irradiated over the photomask 23 for exposure.

Due to the exposure, the exposed portions of the photoresist 22 are solubilized as shown in FIG. 2(C) to form (transfer) the layout pattern on the alloy 21.

Next, the revealed portions of the alloy 21 are removed by aqua regia as shown in FIG. 2(D).

The layout pattern is then etched with hydrogen fluoride into the glass plate 20 as shown in FIG. 2(E).

Next, the photoresist 22 and the alloy 21 are removed to provide the lower substrate 1 as shown in FIG. 2(F).

Next, the upper substrate 4 is prepared (not shown). A method for forming the two through-holes in the upper substrate 4 is not particularly limited. For example, when the material of the upper substrate 4 is glass, an example of the formation method is ultrasonic machining, or the like. For example, when the material of the upper substrate 4 is a polymeric material, examples of the formation method include a cutting method; a molding method (such as injection molding, cast molding and press molding using a metal mold); and like methods. The two through-holes may each be formed separately or may be formed simultaneously. When the two through-holes are formed separately, either hole may be formed earlier. Forming the two through-holes simultaneously by an aforementioned method that uses a metal mold, or a like method requires a small number of steps and is thus preferable.

Figure 2:
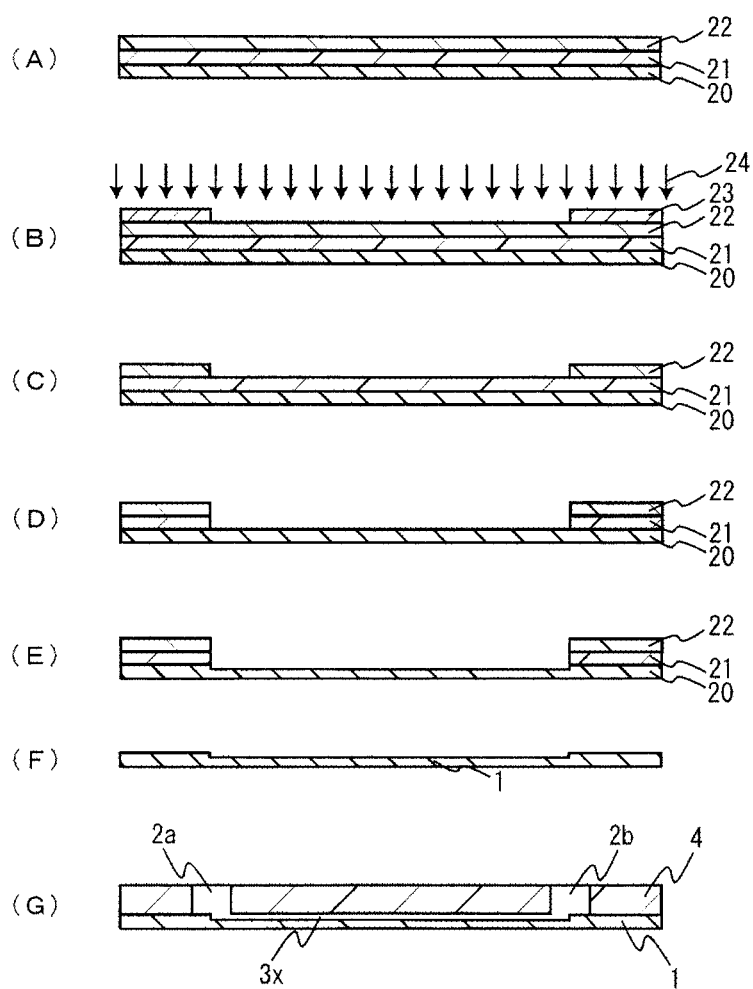
FIG. 2 is a flowchart illustrating an example of a production process of an electrophoresis chip of the present invention.

Finally, by laminating the lower substrate 1 and the upper substrate 4, an electrophoresis chip of this embodiment can be produced. A method for laminating the lower substrate 1 and the upper substrate 4 is not particularly limited and, for example, thermal welding is preferable. FIG. 2 depicts the production process in regard to the cross section shown in FIG. 1 (B).

For example, when the material of the lower substrate 1 is a polymeric material, the electrophoresis chip can be produced as follows.

First, a surface of a silicon plate 31 is coated with a photoresist 32 as shown in FIG. 3(A).

Next, a photosensitive film on which a layout pattern for a capillary channel for sample analysis 3x is drawn is adhered to a surface of the photoresist 32 as shown in FIG. 3(B) to prepare a photomask 33. Irradiation with ultraviolet rays 34 is then performed over the photomask 33 for exposure.

Due to the exposure, the exposed portions of the photoresist 32 are solubilized as shown in FIG. 3(C) to form (transfer) the layout pattern on the silicon plate 31.

Next, the layout pattern is etched into the silicon plate 31 to prepare a base mold 35 as shown in FIG. 3(D). Examples of etching include dry etching, and anisotropic etching, among others. The etching is preferably dry etching in view of the dimensional accuracy and the surface smoothness of the capillary channel for sample analysis 3x.

Metallic nickel electrocasting is then performed on the base mold 35 to prepare a metal mold for injection molding 36 as shown in FIG. 3(E).

Next, a lower substrate 1 composed of polymeric material is prepared by injection molding using the metal mold for injection molding 36 as shown in FIG. 3(F).

Next, the upper substrate 4 is prepared (not shown). A method for preparing the upper substrate 4 is the same as the method used when the material of the lower substrate 1 is glass.

Figure 3:
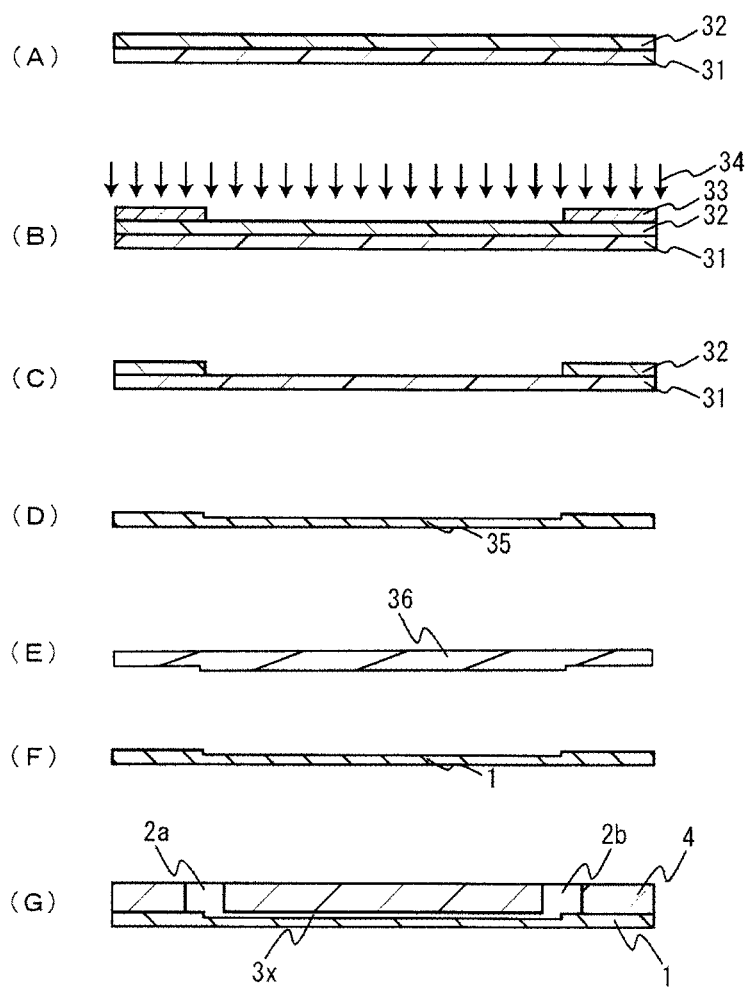
FIG. 3 is a flowchart illustrating another example of a production process of an electrophoresis chip of the present invention.

Finally, by laminating the lower substrate 1 and the upper substrate 4, an electrophoresis chip of this embodiment can be produced. A method for laminating the lower substrate 1 and the upper substrate 4 is the same as the method used when the material of the lower substrate 1 is glass. FIG. 3 depicts the production process in regard to the cross section shown in FIG. 1 (B).

As described above, the introduction reservoir 2a and the recovery reservoir 2b may each include an electrode for use with a capillary electrophoresis method. FIG. 4 shows an electrophoresis chip of this embodiment with electrodes for capillary electrophoresis. In FIG. 4, the portions that are identical to those in FIG. 1 are given the same numbers and symbols. As shown in FIG. 4, in this electrophoresis chip, the introduction reservoir 2a and the recovery reservoir 2b include an electrode 6a for capillary electrophoresis and an electrode 6b for capillary electrophoresis respectively. The electrode 6a for capillary electrophoresis and the electrode 6b for capillary electrophoresis are embedded in the upper substrate 4. The electrode 6a for capillary electrophoresis and the electrode 6b for capillary electrophoresis can be readily positioned by creating, in advance, introduction holes for receiving the electrode 6a for capillary electrophoresis and the electrode 6b for capillary electrophoresis in side surfaces of the upper substrate 4 when producing the upper substrate 4. In an electrophoresis chip of the present invention, the electrodes for capillary electrophoresis are optional components. The electrodes for capillary electrophoresis may be inserted into the introduction reservoir 2a and the recovery reservoir 2b, for example, when the electrophoresis chip is used.

The electrode 6a for capillary electrophoresis and the electrode 6b for capillary electrophoresis may be any electrodes insofar as they are functional in an electrophoresis method. The electrode 6a for capillary electrophoresis and the electrode 6b for capillary electrophoresis are each, for example, a stainless steel (SUS) electrode, a platinum (Pt) electrode, a gold (Au) electrode, or the like.

FIG. 5 shows an example of an electrophoresis apparatus that includes an electrophoresis chip of this embodiment. In FIG. 5, the portions that are identical to those in FIG. 1 and FIG. 4 are given the same numbers and symbols. As shown in FIG. 5, this electrophoresis apparatus includes an analysis unit 7. The analysis unit 7 is disposed on the upper substrate 4 such that it is located between the introduction reservoir 2a and the recovery reservoir 2b over the capillary channel for sample analysis 3x. A light source and a detection unit are housed in the analysis unit 7. The analysis unit 7 emits light toward a sample from the light source and detects light reflected from the sample at the detection unit to measure absorbance. The analysis unit 7 may be anything insofar as it can perform an analysis of a sample, which will be described below. The analysis unit 7 may be composed of, for example, a light source disposed under the electrophoresis chip and a detection unit disposed in a place corresponding to where the analysis unit 7 is disposed. In this case, light is emitted from the light source toward a sample, and light transmitted by the sample is detected at the detection unit to measure absorbance.

In an electrophoresis apparatus (electrophoresis chip) of the present invention, the analysis of glucose in a sample may be carried out by a different method than capillary electrophoresis. The method for analyzing glucose is not limited, and known methods can be selected. A specific example is a method in which a redox reaction is carried out using glucose as a substrate, and the redox reaction is examined to determine glucose. It is preferable in this case that an electrophoresis apparatus (electrophoresis chip) of the present invention further includes a glucose analysis reagent that will be described below. When an electrophoresis apparatus (electrophoresis chip) of the present invention further includes such a glucose analysis reagent, the glucose analysis reagent may be contained in, for example, at least one reservoir among the introduction reservoir, the recovery reservoir and a pretreatment reservoir that will described below. Moreover, an electrophoresis apparatus (electrophoresis chip) of the present invention may further include a reagent reservoir, and the glucose analysis reagent may be contained in the reagent reservoir. It is preferable in this case that the reagent reservoir is in communication with, for example, at least one reservoir among the introduction reservoir, the recovery reservoir and a pretreatment reservoir that will be described below.

Next, specific examples of the glucose analysis reagent are described in combination with a method for analyzing glucose in which the reagent is applied. However, the present invention is not limited thereto.

Firstly, an example of the glucose analysis reagent is a reagent that contains a glucose oxidase, a peroxidase and a chromogenic substrate. For example, a substrate that develops a color due to oxidation is preferable as a chromogenic substrate, such as, for example, sodium N-(carboxymethylaminocarbonyl)-4,4'-bis(dimethylamino)diphenylamine (trade name: DA-64, manufactured by Wako Pure Chemical Industries, Ltd.), 10-(carboxymethylaminocarbonyl)-3,7-bis(dimethylamino)phenothiazine or salts thereof (for example, trade name: DA-67, manufactured by Wako Pure Chemical Industries, Ltd.), hexasodium N,N,N',N',N",N"-hexa(3-sulfopropyl)-4,4',4"-triaminotriphenylmethane (for example, trade name: TPM-PS, manufactured by Dojindo Laboratories), sodium N-(carboxymethylaminocarbonyl)-4,4'-bis(dimethylamino)diphenylamine, orthophenylenediamine (OPD), or a substrate prepared by combining a Trinder's reagent and 4-aminoantipyrine, among others. Examples of Trinder's reagent include phenol, phenol derivatives, aniline derivatives, naphthol, naphthol derivatives, naphthylamine, and naphthylamine derivatives, among others. Moreover, an aminoantipyrine derivative, vanillindiamine sulfonate, methyl benzthiazolinone hydrazone (MBTH), or sulfonated methyl benzthiazolinone hydrazone (SMBTH), among others, can be used in place of 4-aminoantipyrine. When such a glucose analysis reagent is used, glucose can be analyzed, for example, in the following manner. That is, first, a glucose oxidase is reacted with glucose (substrate) to produce glucolactone and hydrogen peroxide. Then, due to catalytic reaction (redox reaction) of a peroxidase that uses the thus-produced hydrogen peroxide and the chromogenic substrate as substrates, the chromogenic substrate is oxidized and develops a color. Because the extent of this color development corresponds to the amount of hydrogen peroxide and because the amount of hydrogen peroxide corresponds to the amount of glucose, quantitative analysis of glucose can be performed indirectly by measuring the color development.

Alternatively, a reagent that contains a redox enzyme and an electrochromic substance can also be mentioned as an example of a glucose analysis reagent. The electrochromic substance is not particularly limited insofar as, for example, the color tone thereof is changed due to the transfer of electrons. Specific examples include viologen, and viologen derivatives, among others.

Examples of viologen derivatives include diphenyl viologen, and dinitrophenyl viologen, among others. Among these, dinitrophenyl viologen is preferable. The electrochromic substances used may be commercially available, or can be prepared by known methods. Examples of the redox enzyme include glucose oxidase (GOD), and glucose dehydrogenase, among others. When such a glucose analysis reagent is used, glucose can be analyzed, for example, in the following manner. That is, glucose is reacted with the redox enzyme in the presence of the electrochromic substance. Due to this enzymatic reaction (redox reaction), electrons are liberated from the glucose. Then, due to the transfer of the liberated electrons to the electrochromic substance, the color tone of the electrochromic substance changes. Because this color-tone change corresponds to the amount of glucose, quantitative analysis of glucose can be performed indirectly by measuring the color-tone change.

Furthermore, a reagent that contains a redox enzyme and a tetrazolium salt having a mediator function can be mentioned as an example of a glucose analysis reagent. Examples of the redox enzyme include those that are identical to the enzymes that can be used in the reagent containing the electrochromic substance. Preferable examples of the tetrazolium salt are those having at least one group from among a nitrophenyl group, a thiazolyl group and a benzothiazolyl group. Examples of tetrazolium salts include 3-(4,5-dimethyl-2-thiazolyl)-2,5-diphenyl-2H-tetrazolium bromide (MTT), 2-(4-iodophenyl)-3-(4-nitrophenyl)-5-phenyl-2H-tetrazolium chloride (INT), 3,3'-[3,3'-dimethoxy-(1,1'-biphenyl)-4,4'-diyl]-bis [2-(4-nitrophenyl)-5-phenyl-2H-tetrazolium chloride] (Nitro-TB), 2-(4-iodophenyl)-3-(4-nitrophenyl)-5-(2,4-disulfophenyl)-2H-tetrazolium monosodium salt (WST-1), 2-(4-iodophenyl)-3-(2,4-dinitrophenyl)-5-(2,4-disulfophenyl)-2H-tetrazolium monosodium salt (WST-3), 2-benzothiazolyl-3-(4-carboxy-2-methoxyphenyl)-5-[4-(2-sulfoethylcarbamoyl)ph enyl]-2H-tetrazolium (WST-4), 2,2'-dibenzothiazolyl-5,5'-bis[4-di(2-sulfophenyl)carbamoylphenyl]-3,3'-(3,3'-dim ethoxy-4,4'-biphenylene) ditetrazolium disodium salt (WST-5), 2-(2-methoxy-4-nitrophenyl)-3-(4-nitrophenyl)-5-(2,4-disulfophenyl)-2H-tetrazoli um monosodium salt (WST-8), 2,3-bis(4-nitrophenyl)-5-phenyltetrazolium chloride, 2-(2-benzothiazolyl)-3,5-dophenyltetrazolium bromide, 2-(2-benzothiazolyl)-3-(4-nitrophenyl)-5-phenyltetrazolium bromide, 2,3-di(4-nitrophenyl)tetrazolium perchlorate, 3-(3-nitrophenyl)-5-methyl-2-phenyltetrazolium chloride, and 3-(4-nitrophenyl)-5-methyl-2-phenyltetrazolium chloride, among others. When such a glucose analysis reagent is used, glucose can be analyzed, for example, in the following manner. That is, glucose is reacted with the redox enzyme in the presence of an aforementioned tetrazolium salt. Due to this enzymatic reaction (redox reaction), electrons are liberated from the glucose. Then, due to the transfer of the liberated electrons to the tetrazolium compound, the tetrazolium compound develops a color. Because the extent of this color development corresponds to the amount of glucose, quantitative analysis of glucose can be performed indirectly by measuring the extent of color development.

A means of measuring the reaction between glucose and the glucose analysis reagent is also not particularly limited, and the measurement can be carried out using a suitable optical measurement instrument. The optical measurement instrument may be a part of an electrophoresis apparatus (electrophoresis chip) of the present invention or may be a separate instrument. The optical measurement instrument is not particularly limited and, for example, a spectrophotometer, a photosensor, a UV spectrometer, or an LED-equipped optical measurement instrument can be used, among others. In an electrophoresis apparatus (electrophoresis chip) of the present invention, the components (such as an enzyme and a substrate) of the glucose analysis reagent (described above) may be disposed, for example, in a mixed state, or each component may be disposed separately and independently.

In the present invention, the method for analyzing glucose may be, for example, an electrode method in addition to the method described above that detects color development that occurs in association with a redox reaction. In the case of an electrode method, it is preferable that an electrophoresis apparatus (electrophoresis chip) of the present invention further includes, for example, electrodes (a cathode and an anode) for use with an electrode method and a glucose analysis reagent, and it is preferable that the electrodes for the electrode method and the glucose analysis reagent are disposed such that they are placed in at least one reservoir among the introduction reservoir, the recovery reservoir and a pretreatment reservoir that will described below. In such an electrophoresis apparatus (electrophoresis chip), glucose can be analyzed by an electrode method, for example, using the electrodes for the electrode method and the glucose analysis reagent. It is more preferable that the electrodes and the glucose analysis reagent are disposed such that they are placed in, for example, at least the introduction reservoir or a pretreatment reservoir that will described below. In an electrophoresis chip of the present invention, the electrodes for the electrode method are optional components. The electrodes for the electrode method may be inserted into at least one reservoir among the introduction reservoir, the recovery reservoir and a pretreatment reservoir that will be described below, for example, when the electrophoresis chip is used. The electrodes for use with an electrode method may be components of, for example, an electrophoresis apparatus of the present invention. A specific example of the glucose analysis reagent that can be used with such an electrode method is described below. However, the present invention is not limited thereto.

An example of the glucose analysis reagent that can be used with the electrode method is a reagent that contains a redox enzyme and an electron acceptor. Examples of the redox enzyme include those identical to the enzymes for use in the reagent (described above) containing an electrochromic substance. Usable examples of an electron acceptor include potassium ferricyanide, p-benzoquinone, phenazine methosulfate, indophenol and derivatives thereof, potassium β-naphthoquinone-4-sulfonate, methylene blue, ferrocene and derivatives thereof, osmium complexes, ruthenium complexes, $NAD^+$, $NADP^+$, and pyrroloquinone (PQQ), among others. When such a glucose analysis reagent is used, glucose can be analyzed, for example, in the following manner. That is, due to the catalytic reaction of the redox enzyme, glucose is oxidized and the electron acceptor is simultaneously reduced. Then, the reduced electron acceptor is reoxidized by an electrochemical technique. Because the oxidation current value obtained from this reoxidation corresponds to the amount of glucose, quantitative analysis of glucose can be performed indirectly by measuring the current. The electrodes for use with an electrode method are not particularly limited, and examples include gold electrodes, carbon electrodes, and silver electrodes, among others. The form of the electrodes is also not particularly limited and, for example, the electrodes may be electrodes in which a GOD enzyme film is fixed onto a film-like substrate surface (glucose electrode film).

Next, a method of the present invention for analyzing a sample is described using as an example the case where the electrophoresis apparatus shown in FIG. 5 is used.

First, the capillary channel for sample analysis 3x is filled with an electrophoresis running buffer by pressure or capillary action. The electrophoresis running buffer is as described above.

When the capillary channel is filled with an electrophoresis running buffer in advance when the electrophoresis apparatus is not in use (when not in analysis), it is possible to omit the step (described above) for filling with an electrophoresis running buffer and to immediately advance to the following steps, and it is thus preferable.

Next, a sample to be analyzed is introduced into the introduction reservoir 2a. At this time, it is preferable to introduce a diluted sample that is diluted so as to have a volume ratio of the sample: the electrophoresis running buffer in a range of 1:4 to 1:99. However, the volume ratio is not limited to this. Next, a voltage is applied to the electrode 6a for capillary electrophoresis and the electrode 6b for capillary electrophoresis to generate a potential difference between both ends of the capillary channel for sample introduction 3x, thereby gradually moving the sample from the introduction reservoir 2a to the recovery reservoir 2b. Examples of the sample include whole blood, hemolyzed samples prepared by subjecting whole blood to a hemolysis treatment, centrifuged blood, spontaneously precipitated blood, and like samples. Examples of hemolysis treatments include sonication treatments, freeze/thaw treatments, pressure treatments, osmotic pressure treatments, and surfactant treatments, among others. For example, when the electrophoresis apparatus (electrophoresis chip) has a pretreatment reservoir that will be described below, the hemolysis treatment may be performed in the pretreatment reservoir. Alternatively, a sample that has been subjected to a hemolysis treatment in advance in a separate apparatus, or the like may be introduced into the electrophoresis apparatus (electrophoresis chip). The sample may be suitably diluted with, for example, water, physiological saline, or a buffer, among others. For example, when the electrophoresis apparatus (electrophoresis chip) has a pretreatment reservoir that will be described below, the dilution may be performed in the pretreatment reservoir. Moreover, a sample that has been subjected to a dilution treatment in advance in a separate apparatus, or the like may be introduced into the electrophoresis apparatus (electrophoresis chip).

The potential difference between the electrode 6a for capillary electrophoresis and the electrode 6b for capillary electrophoresis is in the range of, for example, 0.5 to 5 kV.

Next, the relationship between the absorbance and the time elapsed since the beginning of the application of a voltage to both ends of the capillary channel for sample analysis 3x is measured with the analysis unit 7. Note that an absorbance peak that corresponds to a component present in the sample with a high migration speed appears a short amount of time after the application of voltage is begun, while an absorbance peak that corresponds to a component in the sample with a low migration speed appears a longer amount of time after the application of voltage is begun. It is thus possible to analyze (separate and measure) each component of the sample. Moreover, arithmetic processing (such as differential processing and difference processing) is performed on the absorbance thus measured to give a pherogram, and it is thus possible to determine the proportion of a component in a sample or to determine the extent of separation of the sample by calculating a peak height or a peak area in the pherogram. According to the present invention, it is possible to analyze (separate and measure) the components of the sample (such as glycosylated hemoglobin and other components present in the sample) with high accuracy.

When an electrophoresis apparatus (electrophoresis chip) of this embodiment analyzes glucose by, for example, the electrode method described above, the analysis of glucose is carried out using, for example, a measuring instrument (not shown) as follows. The measuring instrument includes a power source and an ammeter. First, the electrodes (a cathode and an anode) for use with an electrode method are connected to the power source, and the ammeter is disposed between the power source and the electrodes for the electrode method. Next, a voltage is applied to the electrodes. Thereafter, an oxidation current value is measured when the sample reaches a reservoir in which the electrodes and the glucose analysis reagent are disposed. Finally, quantitative analysis of glucose is performed based on the oxidation current value. The measuring instrument may be a part of an electrophoresis apparatus (electrophoresis chip) of the present invention or may be a separate instrument.

When an electrophoresis apparatus (electrophoresis chip) of this embodiment analyzes glucose by, for example, a method that uses the reagent (described above) that develops a color in association with a redox reaction, the analysis of glucose is carried out with, for example, a means that uses an optical measurement instrument as described above. Specifically, the color development (change of color tone) of the reagent is measured when the sample reaches a reservoir in which the reagent is disposed, and quantitative analysis of glucose is performed based on the extent of color development (change of color tone).

In the electrophoresis apparatus (electrophoresis chip), for example, first, glucose may be analyzed (detected), and whether or not to carry out an analysis of glycosylated hemoglobin may be determined based on the amount of glucose detected and other factors thus measured. In this manner, the diagnosis and the like of diabetic complications can be carried out more efficiently. Determination of whether or not to carry out an analysis of glycosylated hemoglobin may be made also in reference to, for example, a flow chart for diabetes diagnosis (classification of disease type). Such determination may be made automatically using, for example, a computer that is connected externally. Moreover, in this case, the type of diabetes as classified by the computer may be output simultaneously with the result of the analysis of glucose.

Moreover, it is also possible to simultaneously analyze glycosylated hemoglobin and glucose by capillary electrophoresis using an electrophoresis apparatus (electrophoresis chip) of this embodiment. In this case, it is preferable from an analysis accuracy point of view that an ionic functional group is introduced into the glucose to produce a glucose derivative.

Embodiment 2

FIG. 6 shows another example of an electrophoresis chip of the present invention. In FIG. 6, the portions that are identical to those in FIG. 1 are given the same numbers and symbols. In an electrophoresis chip of this embodiment, two concave portions and an I-shaped groove are formed in a substrate 1. A surface of the substrate (lower substrate) 1 is sealed with a sealing material (upper substrate) 4 that has openings at places corresponding to the two concave portions. The two concave portions formed in the substrate (lower substrate) 1 serve as an introduction reservoir 2a and a recovery reservoir 2b. By sealing the upper part of the I-shaped groove formed in the substrate (lower substrate) 1 with the sealing material (upper substrate) 4, a capillary channel for sample analysis 3x is formed. Otherwise, an electrophoresis chip of this embodiment is of the same configuration as the electrophoresis chip shown in FIG. 1.

An electrophoresis chip of this embodiment can be produced, for example, as follows. However, the electrophoresis chip may be produced by methods other than the production method described below.

For example, a substrate that is formed from the same material as the lower substrate 1 of the electrophoresis chip shown in FIG. 1 can be used as the substrate (lower substrate) 1.

In an electrophoresis chip of this embodiment, the length and the width of the substrate (lower substrate) 1 correspond to the overall length and the overall width of the chip, as described above. Therefore, the length and the width of the substrate (lower substrate) 1 are arranged to be identical to the overall length and the overall width of the chip, as described above. The thickness of the substrate (lower substrate) 1 in an electrophoresis chip of this embodiment is in a range of, for example, 0.1 to 3 mm and preferably in a range of 1 to 2 mm.

The material of the sealing material (upper substrate) 4 is also not particularly limited and, for example, a substrate that is formed from the same material as the lower substrate 1 of the electrophoresis chip shown in FIG. 1 can be used.

The length and width of the sealing material (upper substrate) 4 are identical to the length and the width of the lower substrate 1, respectively. The thickness of the sealing material (upper substrate) 4 is in a range of, for example, 50 to 1000 μm and preferably in a range of 100 to 300 μm.

For example, a commercially available sealing material may be used for the sealing material (upper substrate) 4 after creating holes in places corresponding to the two concave portions (the introduction reservoir 2a and the recovery reservoir 2b).

In an electrophoresis chip of this embodiment, the overall thickness of the chip is the sum of the thickness of the substrate (lower substrate) 1 and the thickness of the sealing material (upper substrate) 4. The overall thickness of the chip is as described above.

An example of a process for producing an electrophoresis chip of this embodiment is described below. However, the electrophoresis chip may be produced by processes other than the production process described below.

First, the substrate (lower substrate) 1 is prepared. A method for forming the capillary channel for sample analysis 3x in the substrate (lower substrate) 1 is not particularly limited, and the capillary channel may be formed, for example, in the same manner as in Embodiment 1 above. A method for forming the introduction reservoir 2a and the recovery reservoir 2b in the substrate (lower substrate) 1 is also not particularly limited. For example, when the material of the substrate (lower substrate) 1 is glass, an example of a formation method is ultrasonic machining, or the like. For example, when the material of the substrate (lower substrate) 1 is a polymeric material, examples of the formation method include a cutting method; a molding method (such as injection molding, cast molding and press molding using a metal mold); and like methods. The introduction reservoir 2a and the recovery reservoir 2b may each be formed separately or may be formed simultaneously. When the introduction reservoir 2a and the recovery reservoir 2b are formed separately, either reservoir may be formed first. Forming all of the introduction reservoir 2a and the recovery reservoir 2b simultaneously by an aforementioned method that uses a metal mold, or a like method requires a small number of steps and is thus preferable.

Next, by sealing a surface of the substrate (lower substrate) 1 with the sealing material (upper substrate) 4 in which holes are created in places corresponding to the two concave portions (the introduction reservoir 2a and the recovery reservoir 2b), an electrophoresis chip of this embodiment can be produced.

The configuration of an electrophoresis chip of this embodiment is not limited to that shown in FIG. 6. For example, as in FIG. 4 and other figures, a plurality of electrodes may be included, and a pretreatment reservoir that will be described below and the like may suitably be included. The configuration of an electrophoresis apparatus that uses an electrophoresis chip of this embodiment is also not particularly limited and, for example, a detector as in the electrophoresis apparatus of FIG. 5 may be included. Moreover, a method for analyzing a sample using the electrophoresis apparatus is also not particularly limited, and can be carried out, for example, in the same manner as the electrophoresis apparatus shown in FIG. 5 is used.

Embodiment 3

FIG. 7 shows still another example of an electrophoresis chip of the present invention. In FIG. 7, the portions that are identical to those in FIG. 1 are given the same numbers and symbols. In an electrophoresis chip of this embodiment, two through-holes are formed in a substrate (upper substrate) 4. An I-shaped groove is formed in the bottom surface of the substrate (upper substrate) 4. The bottom surface of the substrate (upper substrate) 4 is sealed with a sealing material (lower substrate) 1. The bottom parts of the two through-holes formed in the substrate (upper substrate) 4 are sealed with the sealing material (lower substrate) 1, and thereby an introduction reservoir 2a and a recovery reservoir 2b are formed. By sealing the lower part of the I-shaped groove formed in the substrate (upper substrate) with the sealing material, a capillary channel for sample analysis 3x is formed. Otherwise, an electrophoresis chip of this embodiment is of the same configuration as the electrophoresis chip shown in FIG. 1.

An electrophoresis chip of this embodiment can be produced, for example, as follows. However, the electrophoresis chip may be produced by methods other than the production method described below.

For example, a substrate that is formed from the same material as the lower substrate 1 of the electrophoresis chip shown in FIG. 1 can be used as the substrate (upper substrate) 4.

In an electrophoresis chip of this embodiment, the length and the width of the substrate (upper substrate) 4 correspond to the aforementioned overall length and overall width of the chip, respectively. Therefore, the length and the width of the substrate (upper substrate) 4 are arranged to be identical to the aforementioned overall length and overall width of the chip, respectively. The thickness of the substrate (upper substrate) 4 in an electrophoresis chip of this embodiment is in a range of, for example, 0.1 to 3 mm and preferably in a range of 1 to 2 mm.

The material of the sealing material (lower substrate) 1 is also not particularly limited and, for example, a substrate that is formed from the same material as the lower substrate 1 of the electrophoresis chip shown in FIG. 1 can be used.

The length and the width of the sealing material (lower substrate) 1 are identical to the length and the width of the substrate (upper substrate) 4, respectively. The thickness of the sealing material (lower substrate) 1 is in a range of, for example, 50 to 1000 μm and preferably in a range of 100 to 300 μm.

For example, a commercially available sealing material may be used for the sealing material (lower substrate) 1.

In an electrophoresis chip of this embodiment, the overall thickness of the chip is the sum of the thickness of the substrate (upper substrate) 4 and the thickness of the sealing material (lower substrate) 1. The overall thickness of the chip is as described above.

An example of a process for producing an electrophoresis chip of this embodiment is described below. However, the electrophoresis chip may be produced by processes other than the production process described below.

First, the substrate (upper substrate) 4 is prepared. A method for forming the capillary channel for sample analysis 3x in the substrate (upper substrate) 4 is not particularly limited, and the capillary channel may be formed, for example, in the same manner as in Embodiment 1 above. A method for forming the two through-holes in the substrate (upper substrate) 4 is also not particularly limited, and the through-holes may be formed, for example, in the same manner as in Embodiment 1 above.

Next, by sealing the bottom surface of the substrate (upper substrate) 4 with the sealing material (lower substrate) 1, an electrophoresis chip of this embodiment can be produced.

The configuration of an electrophoresis chip of this embodiment is not limited to that shown in FIG. 7. For example, as in FIG. 4 and other figures, a plurality of electrodes may be included, and a pretreatment reservoir that will be described below and the like may suitably be included. The configuration of an electrophoresis apparatus that uses an electrophoresis chip of this embodiment is also not particularly limited and, for example, a detector as in the electrophoresis apparatus of FIG. 5 may be included. Moreover, a method for analyzing the sample using the electrophoresis apparatus is also not particularly limited, and can be carried out, for example, in the same manner as with the case where the electrophoresis apparatus shown in FIG. 5 is used.

Embodiment 4

FIG. 8 shows still another example of an electrophoresis chip of the present invention. In FIG. 8, the portions that are identical to those in FIG. 1 are given the same numbers and symbols. An electrophoresis chip of this embodiment has a single-piece substrate, and the introduction reservoir and the recovery reservoir are in communication with each other via a capillary tube that is a member independent of the substrate. The capillary tube serves as the capillary channel for sample analysis 3x. The introduction reservoir 2a and the recovery reservoir 2b are each formed as a concave portion in the substrate 1. The substrate 1 has a rectangular parallelepipedic opening (window) 9 more inward in relation to the introduction reservoir 2a and the recovery reservoir 2b. The capillary tube is inserted into the substrate 1 such that one end thereof is placed on the bottom surface of either the introduction reservoir 2a or the recovery reservoir 2b. The substrate 1 is provided with cavities (not shown) for the insertion of both ends of the capillary tube. Otherwise, the electrophoresis chip of this embodiment is of the same configuration as an electrophoresis chip shown in FIG. 1.

An electrophoresis chip of this embodiment can be produced, for example, as follows. However, the electrophoresis chip may be produced by methods other than the production method described below.

For example, a substrate that is formed from the same material as the lower substrate 1 of the electrophoresis chip shown in FIG. 1 can be used as the substrate 1.

In an electrophoresis chip of this embodiment, the length, the width and the thickness of the substrate 1 correspond to the overall length, the overall width and the overall thickness of the chip, as described above. Therefore, the length, the width and the thickness of the substrate 1 are arranged to be identical to the overall length, the overall width and the thickness of the chip, as described above.

The inner diameter of the capillary tube is the same as the diameter of the capillary channel described above. The length of the capillary tube is the same as the length of the capillary channel described above.

An example of a process for producing an electrophoresis chip of this embodiment is described below. However, the electrophoresis chip may be produced by processes other than the production process described below.

First, the substrate 1 is prepared. A method for forming the introduction reservoir 2*a*, the recovery reservoir 2*b* and the opening (window) 9 in the substrate 1 is not particularly limited and, for example, they can be formed by the same method as used for the introduction reservoir 2*a* and the recovery reservoir 2*b* of the electrophoresis chip shown in FIG. 6. The introduction reservoir 2*a*, the recovery reservoir 2*b* and the opening (window) 9 may each be formed separately or may all be formed simultaneously. When the introduction reservoir 2*a*, the recovery reservoir 2*b* and the opening (window) 9 are formed separately, they may be formed in any order. Forming all of the introduction reservoir 2*a*, the recovery reservoir 2*b* and the opening (window) 9 simultaneously by an aforementioned method that uses a metal mold, or a like method requires a small number of steps and is thus preferable.

Next, the capillary tube is inserted into the substrate 1 such that both ends thereof are placed on the bottom surfaces of the introduction reservoir 2*a* and the recovery reservoir 2*b*, respectively. In this manner, an electrophoresis apparatus of this embodiment can be obtained.

FIG. 9 shows an electrophoresis chip of this embodiment in which electrodes for use with a capillary electrophoresis method are provided. In FIG. 9, parts that are identical to those shown in FIG. 4 are given the same numbers and symbols. As shown in FIG. 9, the electrode 6*a* for capillary electrophoresis and the electrode 6*b* for capillary electrophoresis are embedded in the substrate 1 in this electrophoresis chip. Otherwise, an electrophoresis chip of this embodiment is of the same configuration as the electrophoresis chip shown in FIG. 4. The electrode 6*a* and the electrode 6*b* can be readily disposed in position by creating, in advance, introduction holes for receiving the electrode 6*a* for capillary electrophoresis and the electrode 6*b* for capillary electrophoresis in side surfaces of the substrate 1 when producing the upper substrate 1.

FIG. 10 shows an example of an electrophoresis apparatus that includes an electrophoresis chip of this embodiment. In FIG. 10, the portions that are identical to those in FIG. 5 are given the same numbers and symbols. As shown in FIG. 10, an analysis unit 7 is directly disposed on the capillary tube in this electrophoresis apparatus. Otherwise, an electrophoresis apparatus of this embodiment has the same configuration as the electrophoresis apparatus shown in FIG. 5. An analysis of a sample using an electrophoresis apparatus of this embodiment can be carried out in the same manner as with the case where the electrophoresis apparatus shown in FIG. 5 is used.

Embodiment 5

Figure 11:
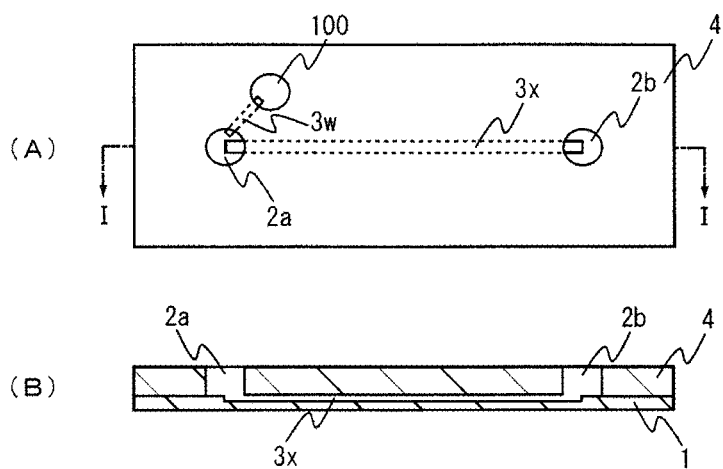
FIG. 11 shows diagrams illustrating a configuration of still another example of an electrophoresis chip of the present invention.

FIG. 11 shows still another example of an electrophoresis chip of the present invention. In FIG. 11, the portions that are identical to those in FIG. 1 are given the same numbers and symbols. As shown in FIG. 11, this electrophoresis chip is provided with a pretreatment reservoir 100 where the pretreatment of the sample is carried out near the introduction reservoir 2*a*. The pretreatment reservoir 100 is in communication with the introduction reservoir 2*a* via a channel 3*w* that is independent of the capillary channel for sample analysis 3*x*. Otherwise, the configuration of an electrophoresis chip of this embodiment is the same as the electrophoresis chip of FIG. 1. Moreover, the configuration of an electrophoresis chip of this embodiment is not limited thereto. For example, the electrophoresis chip may be composed of a single-piece substrate as in the electrophoresis chip of FIG. 8. Moreover, when there is a pretreatment reservoir 100 provided and glucose is analyzed by the electrode method, for example, the pretreatment reservoir 100 in addition to, or in place of, at least one reservoir of the introduction reservoir 2*a* and the recovery reservoir 2*b* (for example, the introduction reservoir 2*a*) may include the electrodes (a cathode and an anode) for use with an electrode method and the glucose analysis reagent.

A method for producing an electrophoresis chip of this embodiment is also not particularly limited, and may be identical to, for example, the production methods described in Embodiments 1 through 4 above. The configuration of an electrophoresis apparatus that uses an electrophoresis chip of this embodiment is also not particularly limited and, for example, a detector as in the electrophoresis apparatus of FIG. 5 or FIG. 10 may be included.

An analysis method that uses an electrophoresis apparatus of this embodiment is also not particularly limited, and can be carried out, for example, as follows. That is, firstly, a sample is introduced into the pretreatment reservoir 100. The sample after being pretreated is introduced into the introduction reservoir 2*a* via the channel 3*w* that connects the pretreatment reservoir 100 and the introduction reservoir 2*a*. The sample is hemolyzed and diluted in the pretreatment reservoir 100. Such hemolysis treatment of the sample is not particularly limited and, for example, it may be a treatment in which the sample is hemolyzed with a hemolytic agent. The hemolytic agent destroys, for example, the blood cell membrane of a blood cell component present in the sample that will be described below. Examples of hemolytic agents include electrophoresis running buffers (described above), saponin, and "Triton X-100" (trade name) manufactured by Nacalai Tesque, Inc., among others, with an electrophoresis running buffer being particularly preferable. Such a method for moving the sample between the pretreatment reservoir 100 and the introduction reservoir 2*a* is also not limited and, for example, the sample may be moved by using an internal pressure difference, potential difference, or the like in each channel. The method for creating such an internal pressure difference, potential difference, or the like is not particularly limited, and examples may be a method that connects a pump or a voltage applying means to both ends of each channel, a method that uses a micro valve, or like methods.

Next, a potential difference is created between both ends of the capillary channel for sample analysis 3*x* in the same manner as with the analysis method that uses the analysis apparatus of FIG. 5 or FIG. 10, thereby moving the sample from the introduction reservoir 2*a* to the recovery reservoir 2*b*, and the sample is analyzed with the analysis unit 7 during this movement.

Embodiment 6

Figure 12:
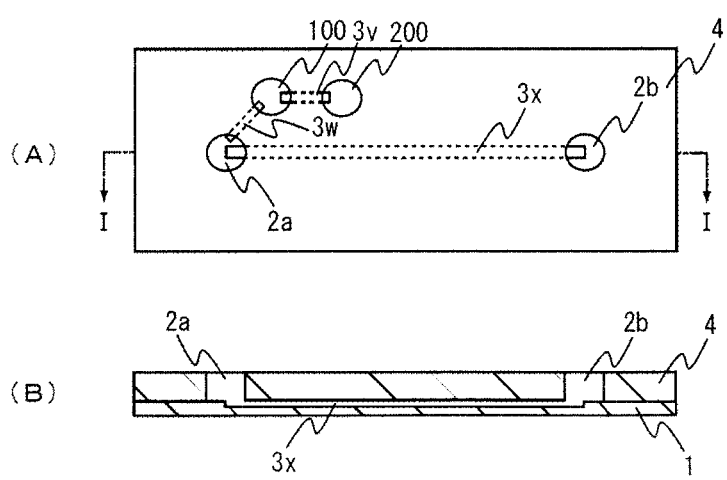
FIG. 12 shows diagrams illustrating a configuration of still another example of an electrophoresis chip of the present invention.

FIG. 12 shows still another example of an electrophoresis chip of the present invention. In FIG. 12, the portions that are identical to those in FIG. 11 are given the same numbers and symbols. As shown in FIG. 12, this electrophoresis chip is provided with a reagent reservoir 200 that contains a glucose analysis reagent near the pretreatment reservoir 100. The glucose analysis reagent is identical to the glucose analysis reagent (described above) containing a reagent that develops a color in association with a redox reaction. The reagent reservoir 200 is in communication with the pretreatment reservoir 100 via a channel 3v that is independent of the capillary channel for sample analysis 3x. The reagent reservoir 200 is not in direct communication with the introduction reservoir 2a. Otherwise, the configuration of the electrophoresis chip of FIG. 12 is the same as that of the electrophoresis chip in FIG. 11.

A method for producing an electrophoresis chip of this embodiment is also not particularly limited, and may be identical to, for example, the production methods described in Embodiments 1 through 4 above. The configuration of an electrophoresis apparatus that uses an electrophoresis chip of this embodiment is also not particularly limited and, for example, a detector as in the electrophoresis apparatus of FIG. 5 or FIG. 10 may be included. An analysis method using an electrophoresis apparatus of this embodiment is not particularly limited and, for example, it can be carried out in the same manner as with an electrophoresis apparatus using the electrophoresis chip of FIG. 11 except that the sample is moved from the pretreatment reservoir 100 to the reagent reservoir 200 during the course of operation and glucose is analyzed in the reagent reservoir 200.

Embodiment 7

Figure 13:
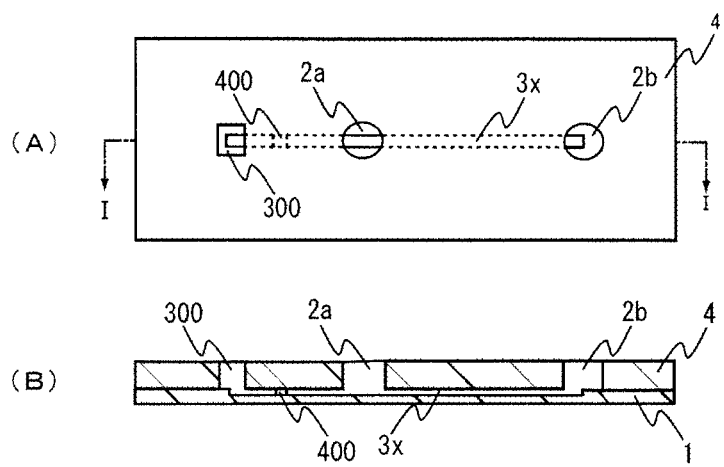
FIG. 13 shows diagrams illustrating a configuration of still another example of an electrophoresis chip of the present invention.

FIG. 13 shows still another example of an electrophoresis chip of the present invention. In FIG. 13, the portions that are identical to those in FIG. 1 are given the same numbers and symbols. As shown in FIG. 13, this electrophoresis chip has a glucose analysis unit 300 at one end of the capillary channel for sample analysis 3x. The recovery reservoir 2b is disposed at the other end of the capillary channel for sample analysis 3x. The introduction reservoir 2a is disposed between the glucose analysis unit 300 and the recovery reservoir 2b. The glucose analysis unit 300 and the introduction reservoir 2a, as well as the introduction reservoir 2a and the recovery reservoir 2b, are in communication via the capillary channel for sample analysis 3x. A draining area 400 is formed in a place between the introduction reservoir 2a and the glucose analysis unit 300 in the capillary channel for sample analysis 3x. The configuration of the glucose analysis unit 300 is not particularly limited, and the glucose analysis unit 300 may contain, for example, electrodes (a cathode and an anode) for use with an electrode method and a glucose analysis reagent, or a glucose analysis reagent (described above) that develops a color in association with a redox reaction. Otherwise, the configuration of an electrophoresis chip of this embodiment is the same as that of the electrophoresis chip of in FIG. 1. Moreover, the configuration of an electrophoresis chip of this embodiment is not limited to this. For example, the electrophoresis chip may be composed of a single-piece substrate as with the electrophoresis chip of FIG. 8.

A method for producing an electrophoresis chip of this embodiment is also not particularly limited, and may be identical to, for example, the production methods described in Embodiments 1 through 4 above. The configuration of an electrophoresis apparatus that uses an electrophoresis chip of this embodiment is also not particularly limited and, for example, a detector as in the electrophoresis apparatus of FIG. 5 or FIG. 10 may be provided between the introduction reservoir 2a and the recovery reservoir 2b on the capillary channel for sample analysis 3x.

An analysis method that uses an electrophoresis apparatus of this embodiment is also not particularly limited, and can be carried out, for example, as follows. That is, firstly, a sample is introduced into the introduction reservoir 2a. The method of sample introduction is not particularly limited and, for example, a pump, a micro valve, or the like can be used. The sample is moved to the glucose analysis unit 300, and glucose is analyzed with the glucose analysis unit 300. The method of glucose analysis is not particularly limited and, for example, an electrode method, or a measurement of the color development (color-tone change) of a reagent that develops a color in association with a redox reaction, or other like methods can be suitably used by the configuration of the glucose analysis unit 300. The method for moving the sample from the introduction reservoir 2a to the glucose analysis unit 300 is also not particularly limited and, for example, it may be a method that creates an internal pressure difference by connecting a pump to both ends of each channel, or it may be a method that applies a voltage, or a like method. Then, a potential difference is created between both ends of the capillary channel for sample analysis 3x in the same manner as with the analysis method that uses the analysis apparatus of FIG. 5 or FIG. 10, thereby moving the sample from the introduction reservoir 2a to the recovery reservoir 2b, and the sample is analyzed during this movement with a measurement unit as in the electrophoresis apparatuses of FIG. 5 and FIG. 10.

EXAMPLES

Example 1

An electrophoresis chip as shown in FIG. 1 was produced by the method described above. This electrophoresis chip was made from PMMA and had a length (dimension in a direction parallel to the capillary channel for sample analysis 3x) of 70 mm and a width of 30 mm. The distance from the center of the introduction reservoir 2a to the center of the recovery reservoir 2b was 46 mm, and the length (overall length) of the capillary channel for sample analysis 3x was 40 mm. The capillary channel for sample analysis 3x had a width and a depth of 40 µm, being a square.

Next, an electrophoresis apparatus as shown in FIG. 5 was formed using this electrophoresis chip, and HbA1c was analyzed using the apparatus. That is, firstly, an electrophoresis running buffer was used to fill the capillary channel for sample analysis 3x by capillary action. For the electrophoresis running buffer, 100 mM fumaric-Arg+0.8% chondroitin (pH 4.8) was used.

Next, a sample was introduced into the introduction reservoir 2a. For the sample, 5 mg/mL Hb (HbA1c content: 10.5 mass % (commercially available control (manufactured by BML)) was used. Then, a voltage of 1 kV was applied to the electrode 6a and no voltage was applied to the electrode 6b, thereby creating a potential difference between both ends of the capillary channel for sample introduction 3x. Thereby, the sample was moved from the introduction reservoir 2a toward the recovery reservoir 2b side. In this instance, the relationship between absorbance and the time that had elapsed since the beginning of the application of the voltage to both ends of the capillary channel for sample analysis 3x was measured with the analysis unit 7. The length of the portion from the introduction reservoir to the analysis unit 7 of the capillary channel for sample analysis 3x (partial length) was 20 mm. The specific configuration of the glucose analysis unit 7 was such that the capillary channel for sample analysis 3x was irradiated from below by an LED, and the absorbance was measured with a photodiode.

Example 2

An electrophoresis chip as shown in FIG. 8 was produced by the method described above. This electrophoresis chip was made from PMMA, and the capillary channel for sample analysis 3x was prepared by embedding a glass capillary tube in it. This electrophoresis chip had a length (dimension in a direction parallel to the capillary channel for sample analysis 3x) of 76 mm and a width of 26 mm. The distance from the center of the introduction reservoir 2a to the center of the recovery reservoir 2b was 46 mm, and the length (overall length) of the capillary channel for sample analysis 3x was 40 mm. The capillary channel for sample analysis 3x had an inner diameter of 50 µm, having a circular cross-section.

An electrophoresis apparatus as shown in FIG. 10 was produced using this electrophoresis chip, and HbA1c was analyzed using the apparatus in the same manner as in Example 1. The length of the portion from the introduction reservoir to the analysis unit 7 of the capillary channel for sample analysis 3x (partial length) was 20 mm.

Figure 14:
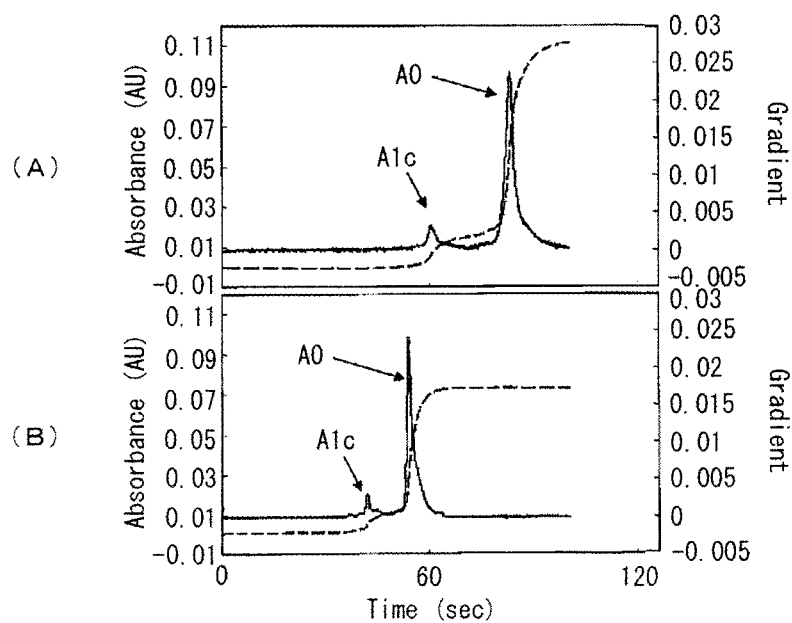
FIG. 14 shows graphs depicting the results of the analyses in the Examples.

The results of Examples 1 and 2 are shown together in the graphs of FIG. 14. In FIG. 14, the graph (A) shows the result for Example 2 and the graph (B) shows the result for Example 1. In FIG. 14, the vertical axes indicate absorbance (relative value, AU) and inclination, and the horizontal axes indicate the time elapsed from the first application of voltage to both ends of the capillary channel for sample analysis 3x. In FIG. 14, a broken line indicates measured absorbance, and a solid line indicates an inclination value obtained after differential processing of the absorbance. In FIG. 14, "A0" and "A1c" indicate an HbA0 peak and an HbA1c peak, respectively. As shown in FIG. 14, it was possible in the Examples to efficiently separate HbA1c from HbA0 present in the samples in a short period of time and to measure HbA1c and HbA0 with high accuracy.

INDUSTRIAL APPLICABILITY

An electrophoresis chip of the present invention can be small and simple and enables a sample to be analyzed with high accuracy. In addition, due to its simple structure, an electrophoresis chip of the present invention also simplifies analysis and shortens the analysis time. An electrophoresis chip of the present invention is applicable to all technical fields where a sample is analyzed, such as laboratory tests, biochemical examinations and medical research. The intended use of the electrophoresis chip is not limited and it is applicable to a broad range of technical fields.

The invention claimed is:

1. A method for analyzing a sample according to a capillary electrophoresis method using an electrophoresis chip, wherein the electrophoresis chip comprises
    a substrate,
    an introduction reservoir,
    a recovery reservoir and
    a capillary channel,
    the capillary channel comprising a capillary channel for sample analysis,
    the introduction reservoir and the recovery reservoir being formed in the substrate,
    the introduction reservoir and the recovery reservoir being in communication with each other via the capillary channel for sample analysis, and
    the introduction reservoir receiving a sample to be analyzed,
the method comprising:
    an introduction step of introducing the sample into the introduction reservoir,
    where the sample is diluted with an electrophoresis running buffer and then introduced into the introduction reservoir, and the sample: the electrophoresis running buffer volume ratio is in a range of 1:4 to 1:99, and
    an analysis step of electrophoretically introducing the sample directly into the capillary channel for sample analysis by creating a potential difference between the introduction reservoir and the recovery reservoir, and also analyzing the sample in the capillary channel during separation of the sample while the sample is being continuously supplied to the capillary channel for sample analysis,
    wherein, in the analysis step, the analysis of the sample is carried out by arithmetic processing of an absorbance of the sample, the sample containing at least glycosylated hemoglobin or glucose, where the arithmetic processing is differential processing to give a pherogram, and the proportion of a component in the sample is obtained by obtaining at least a peak area in the pherogram.

2. The analysis method according to claim 1, wherein the capillary channel is filled with an electrophoresis running buffer.

3. The analysis method according to claim 1, wherein the capillary channel has a diameter in a range of 10 to 200 µm and a length of 0.5 to 15 cm.

4. The analysis method according to claim 1, wherein
    the sample is whole blood,
    the electrophoresis chip further comprises a pretreatment reservoir for hemolyzing the sample with a hemolyzing agent and for diluting the sample, and
    the pretreatment reservoir and the introduction reservoir are in fluid and electrical communication with each other.

5. The analysis method according to claim 1, wherein
    a glucose analysis unit is formed at one end of the capillary channel for sample analysis,
    the recovery reservoir is formed at the other end of the capillary channel for sample analysis,
    the introduction reservoir is formed between the glucose analysis unit and the recovery reservoir, and
    the glucose analysis unit and the introduction reservoir are in fluid and electrical communication, and the introduction reservoir and the recovery reservoir are in fluid and electrical communication, via the capillary channel for sample analysis.

6. The analysis method according to claim 1, wherein
    the substrate comprises an upper substrate and a lower substrate,
    two through-holes are formed in the upper substrate,
    a groove is formed in the lower substrate,
    the upper substrate is laminated onto the lower substrate, spaces created by sealing the bottom parts of the two through-holes formed in the upper substrate with the lower substrate serve as the introduction reservoir and the recovery reservoir, and a space created by sealing the upper part of the groove formed in the lower substrate with the upper substrate serves as the capillary channel for sample analysis.

7. The analysis method according to claim 1, wherein two concave portions and a groove are formed in the substrate, a surface of the substrate is sealed with a sealing material that has openings at places corresponding to the two concave portions, the two concave portions formed in the substrate serve as the introduction reservoir and the recovery reservoir, and a space created by sealing the upper part of the groove formed in the substrate with the sealing material serves as the capillary channel for sample analysis.

8. The analysis method according to claim 1, wherein a sealing material is further included, two through-holes are formed in the substrate, a groove is formed in the bottom surface of the substrate, the bottom surface of the substrate is sealed with the sealing material, spaces created by sealing the bottom parts of the two through-holes formed in the substrate with the sealing material serve as the introduction reservoir and the recovery reservoir, and a space created by sealing the lower part of the groove formed in the bottom surface of the substrate with the sealing material serves as the capillary channel for sample analysis.

9. The analysis method according to claim 1, wherein the introduction reservoir and the recovery reservoir each has a volume in a range of 1 to 1000 mm$^3$.

10. The analysis method according to claim 1, wherein the introduction reservoir and the recovery reservoir each has an electrode for use with a capillary electrophoresis method.

11. A method for analyzing a sample according to a capillary electrophoresis method using an electrophoresis apparatus, wherein the electrophoresis apparatus comprises an electrophoresis chip and an analysis unit, wherein the electrophoresis chip comprises a substrate, an introduction reservoir, a recovery reservoir and a capillary channel, the capillary channel comprising a capillary channel for sample analysis, the introduction reservoir and the recovery reservoir being formed in the substrate, the introduction reservoir and the recovery reservoir being in communication with each other via the capillary channel for sample analysis, and the introduction reservoir receiving a sample to be analyzed, the method comprising:

an introduction step of introducing the sample into the introduction reservoir, and an analysis step of electrophoretically introducing the sample directly into the capillary channel for sample analysis by creating a potential difference between the introduction reservoir and the recovery reservoir, and also analyzing the sample in the capillary channel during separation of the sample while the sample is being continuously supplied to the capillary channel for sample analysis, wherein, in the analysis step, the analysis of the sample is carried out by arithmetic processing of an absorbance of the sample, the sample containing at least glycosylated hemoglobin or glucose, where the arithmetic process is differential processing to give a pherogram, and the proportion of a component in the sample is obtained by obtaining at least a peak area in the pherogram, and wherein, in the introduction step, a diluted sample in which the sample is diluted with an electrophoresis running buffer is introduced into the introduction reservoir, and the volume ratio of the sample: the electrophoresis running buffer is in a range of 1:4 to 1:99.

* * * * *